(12) United States Patent
Qiao et al.

(10) Patent No.: US 7,074,622 B2
(45) Date of Patent: Jul. 11, 2006

(54) METHOD AND SYSTEM FOR SORTING AND SEPARATING PARTICLES

(75) Inventors: Tiecheng A. Qiao, Webster, NY (US); Yun C. Chang, Rochester, NY (US); Eric R. Schmittou, Rochester, NY (US); Thomas I. Penner, Fairport, NY (US)

(73) Assignee: Eastman Kodak Company, Rochester, NY (US)

( * ) Notice: Subject to any disclaimer, the term of this patent is extended or adjusted under 35 U.S.C. 154(b) by 40 days.

(21) Appl. No.: 10/988,920

(22) Filed: Nov. 15, 2004

(65) Prior Publication Data

US 2006/0105350 A1    May 18, 2006

(51) Int. Cl.
*G01N 33/543* (2006.01)
*G01N 33/532* (2006.01)
*G01N 33/53* (2006.01)
*C07C 39/04* (2006.01)
*C09D 189/00* (2006.01)

(52) U.S. Cl. .................. 436/518; 436/524; 436/527; 436/544; 436/824; 435/7.1; 435/7.97; 435/7.91; 568/362; 530/812; 106/160.1

(58) Field of Classification Search ............... 435/518, 435/7.1, 7.9, 7.91; 436/524, 527, 544, 824; 568/362; 530/812; 106/160.1
See application file for complete search history.

(56) References Cited

U.S. PATENT DOCUMENTS

| 4,782,023 | A | 11/1988 | Anawis et al. |
| 4,962,029 | A | 10/1990 | Levenson et al. |
| 5,182,376 | A | 1/1993 | Edwards et al. |
| 5,650,324 | A | 7/1997 | Gorman et al. |
| 5,776,714 | A | 7/1998 | Snoke |
| 5,792,618 | A | 8/1998 | Starkweather et al. |
| 5,981,180 | A | 11/1999 | Chandler et al. |
| 5,989,842 | A | 11/1999 | Schmidt et al. |
| 6,023,540 | A | 2/2000 | Walt et al. |
| 6,162,610 | A | 12/2000 | Bronstein et al. |
| 2003/0068609 | A1 | 4/2003 | Chari et al. |

FOREIGN PATENT DOCUMENTS

| WO | WO 90/11525 | * 10/1990 |
| WO | 02/078906 A2 | 10/2002 |

OTHER PUBLICATIONS

Co-pending U.S. Appl. No. 10/989,072, Qiao et al., Method and system for multiple biological analytes detectioin (D-87468).
Co-pending U.S. Appl. No. 10/989,062, Qiao et al., Method and system for nucleic acid detection (D-87466).
M. Han, X. Gao, J.Z. Su and S. Nie, *Quantum-dot-tagged microbeads for multiplexed optical coding of biomolecules*, Nature Biotech. vol. 19, pp. 631-635 (2001).

* cited by examiner

*Primary Examiner*—Long V. Le
*Assistant Examiner*—Shafiqul Haq
(74) *Attorney, Agent, or Firm*—Lynne M. Blank

(57) ABSTRACT

The present invention relates to a method of particle separation comprising preparing a suspension of particles containing at least one recognizable target particle in a suspending solution, labeling the target particle with a conjugate marker, wherein the conjugate marker comprises at least one recognition unit for the recognizable target particle and at least one peroxidase enzyme, contacting a gelatin surface with the suspending solution, adding developer to the suspending solution in contact with the gelatin surface and in the presence of phenol to attach the target particle to the gelatin surface, and washing the gelatin surface to remove unattached particles. The method may also include detecting the presence of the target particle on the gelatin surface as well as detaching and recovering the attached particles after removal of the non-target particles.

48 Claims, 3 Drawing Sheets

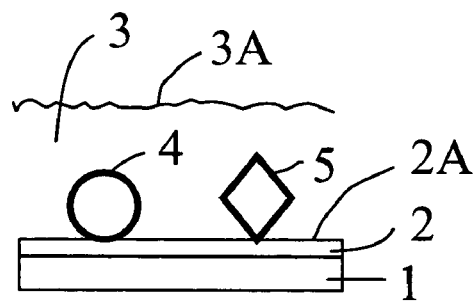
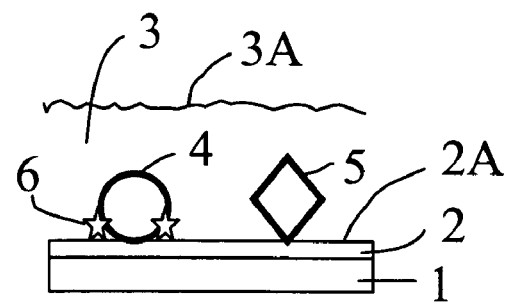
Fig. 1A    Fig. 1B
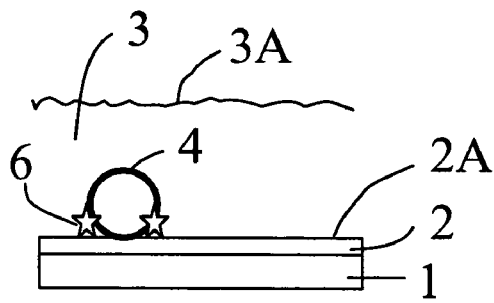
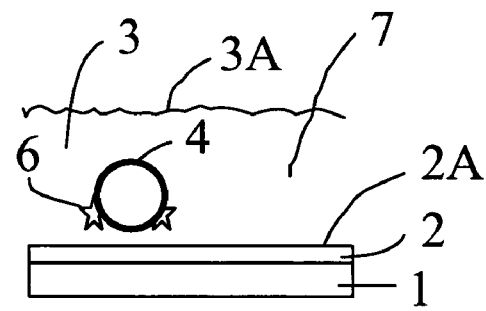
Fig. 1C    Fig. 1D

METHOD AND SYSTEM FOR SORTING AND SEPARATING PARTICLES

CROSS REFERENCE TO RELATED APPLICATIONS

Reference is made to commonly assigned, co-pending U.S. patent applications:

Ser. No. 10/989,072 by Qiao et al. filed of even date herewith entitled "Method For Sensitive Detection Of Multiple Biological Analytes"; and Ser. No. 10/989,062 by Qiao et al. filed of even date herewith entitled "Method And System For Nucleic Acid Detection", the disclosures of which are incorporated herein.

FIELD OF THE INVENTION

The present invention relates generally to the field of methods and devices for sorting and/or separating particles and more specifically to methods and devices based on adherence of surface tagged particles to gelatin coated substrates.

BACKGROUND OF THE INVENTION

The separation and sorting of particles having different properties has many valuable industrial, medical, pharmaceutical, diagnostic, and scientific applications. Various methods and devices for the separation and/or sorting of particles based on differences in physical or chemical properties of the particles are known in the art. For example, methods for separating or sorting living cells, sub-cellular components and organelles, macromolecules, molecular complexes, or multimolecular aggregates of biological or synthetic origin are often required in the fields of biotechnology, medicine, diagnostic testing, drug development, and drug screening. Such sorting or separation methods may include centrifugation methods, density gradient separation methods, magnetic-based separation methods, flow cytometry (FC) methods, and fluorescence assisted cell sorting (FACS) methods. The two leading methods in quality cell separation are flow cytometry and magnetic separation. In flow cytometry, cells are marked with fluorescent tags and passed single-file through a measuring apparatus, deflecting cells on the basis of the their markers. This method is efficient, however remains limited in specificity. It is also time consuming, and the apparatus required is highly expensive. Similarly, magnetic separation involves tagging the desired cells with magnetic particles, causing these cells to adhere to regions of high magnetic field. While this method can process large quantities of cells at once and is therefore much more time efficient in comparison with flow cytometry, it offers low selectivity and high cost, although significantly less expensive than flow cytometry systems. WO 02/078906 A2 discloses a method and device for sorting and separating particles based on selective adherence of particle on metal grain, such as silver halide, coated light sensitive surface by irradiation of specific location a particle residing followed by a photochemical development process. However, the disclosed process requires a light tight device and involves a complicated process to operate. New separation methods are necessary that will increase the specificity of cells to be separated, while maintaining high selectivity and providing affordable and simple equipment to a broader market range.

Problem to be Solved

The problem to be solved is a method for the separation and sorting of particles, in particularly bio-particles, e.g. mammalian cells, which can be very useful in medical, pharmaceutical, diagnostic, and scientific applications.

SUMMARY OF THE INVENTION

The present invention relates to a method of particle separation comprising preparing a suspension of particles containing at least one recognizable target particle in a suspending solution, labeling the target particle with a conjugate marker, wherein the conjugate marker comprises at least one recognition unit for the recognizable target particle and at least one peroxidase enzyme, contacting a gelatin surface with the suspending solution, adding developer to the suspending solution in contact with the gelatin surface and in the presence of phenol to attach the target particle to the gelatin surface, and washing the gelatin surface to remove unattached particles. The method may also include detecting the presence of the target particle on the gelatin surface as well as detaching and recovering the attached particles after removal of the non-target particles.

ADVANTAGEOUS EFFECT OF THE INVENTION

The present invention includes several advantages, not all of which are incorporated in a single embodiment. The present invention provides a method for fast, simple, and inexpensive disease prognosis and diagnosis. The invention is particularly useful for sorting and detecting specific cells for disease diagnosis.

BRIEF DESCRIPTION OF THE DRAWINGS

FIGS. 1A–1D are schematic diagrams illustrating a particle sorting and separation process.

DETAILED DESCRIPTION OF THE INVENTION

Figure 2:
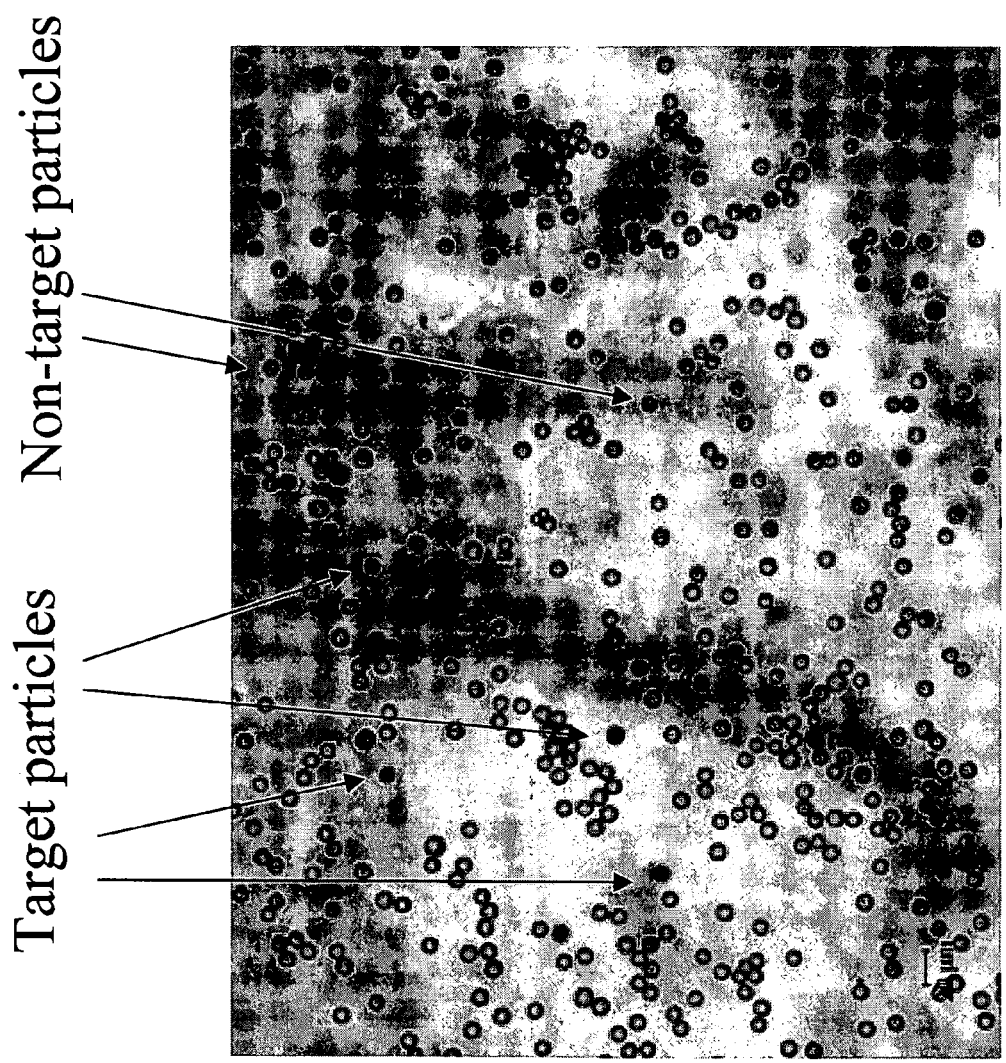
FIG. 2 shows a microscopic image of two different types of particles, non-target particles-white (light), and target particles-magenta (dark), before separation.

The present invention is a novel method for sorting and/or separating particles. The method is generally based on the selective immobilization of at least one type of particle or particles in a mixture of particles on a coated surface through a chemical binding process. The particle or particles to be separated adhere or bind to the surface and become immobilized due to physical or chemical interactions with the surface. The separation may then be completed by washing the surface to remove any non-adhering (non-immobilized) particles in the mixture of particles.

This invention provides a composition and method for selectively sorting and separating particles with distinguishable surface markers, e.g. an antigen on a mammalian cell surface, that can be specifically recognized by a recognition unit, e.g. an antibody or ligand. It comprises a) a surface coated with gelatin; b) an aqueous solution containing a phenolic compound in which a mixture of marked or identifiable/recognizable particles is suspended; c) a conjugate marker containing a recognition unit and a peroxidase in which the recognition unit has high specific affinity to the marked surface of the particle to be separated. The method of sorting and separating consists of 1) suspending a mixture of marked or identifiable/recognizable particles in an aqueous solution containing a phenolic compound and a recognition unit-peroxidase conjugate; 2) pouring the suspension onto a gelatin coated surface; 3) adding a developer, such as hydrogen peroxide, to the suspension spread on the gelatin surface; 4) washing the gelatin surface to remove unattached particles; 5) detaching the separated particles from the gelatin surface. The invention is particularly useful for sorting and separating bioparticles such as immunocytes, stem cells, and cancer cells. The invention has significant implications for diagnosis of diseases.

The target particles in this invention can be inorganic or organic particles, living or non-living cells (dead cells, fixed or non-fixed), which may include eukaryotic cells and prokaryotic cells, mammalian cells, bacteria, cellular aggregates, various sub-cellular organelles, or sub-cellular target particles, including such target particles as proteins and nucleic acids. The target particles can be circular or spherical, square, elliptical, or any other shape. The target particles to be sorted or separated have to be identifiable or recognizable from any other particles which may be present. The term "target particle" means the particles to be sorted or separated from a mixture of at least two different types of particles. The target particle may also be recognizable or identifiable by characteristics of the particles themselves, as in the case of an antigen. Target particles may be labeled with a specific marker in an aqueous or non-aqueous suspension directly or indirectly. The term "marker" in this invention means a molecule or a molecular assembly that has a distinguishable higher binding affinity to the target particle or particles than to the non-target particles.

The conjugate marker in this invention consists of at least two parts; 1) a recognition unit for the target particle; 2) a peroxidase enzyme. The recognition unit recognizes the target particle in a specific manner and binds to the target particle strongly. Typically the recognition unit should have an affinity constant to the target particle of no less than $10^{-6}M^{-1}$. For living cell sorting applications, some commonly used recognition units should be able to recognize specific cell surface molecules. Examples of such recognition units include, but are not limited to, antibodies, antigens, ligands for cell surface receptors, etc. Antibodies are a class of naturally occurring protein molecules that are capable of binding targets with high affinity and specificity. The properties and protocols of using antibodies can be found in "*Using Antibodies; A Laboratory Manual*", (Cold Spring Harbor Laboratory Press, by Ed Harlow and David Lane, Cold Spring Harbor, N.Y. 1999). Antigens can also be used as recognition units if antibodies are the intended cell surface targets. Protein scaffolds such as whole protein/enzyme or their fragments can be used as recognition units as well. In another embodiment of the invention, the nucleic acid probe can be any protein scaffold or synthetic molecular moiety capable of recognizing a specific DNA sequence, as described, for example, in U.S. Pat. Appl. Publ. 2003/0170474; 2003/0162181; 2003/0143549, incorporated herein by reference. Examples include phosphotases, kinases, proteases, oxidases, hydrolyases, cytokines, or synthetic peptides. Nucleic acid ligands can be used as recognition units. A strong binding nucleic acid recognition unit can be obtained through in vitro selection and enrichment for their binding affinity and specificity to certain targets.

The principle of such a selection process can be found in Science, Vol. 249, 505–510, 1990 and Nature, Vol. 346, 818–822, 1990.

U.S. Pat. No. 5,110,833 discloses an alternative class of synthetic molecules that can mimic antibody binding affinity and specificity and can be readily prepared by the so-called Molecular Imprinting Polymer (MIP). This technology has been reviewed in *Chem. Rev. Vol.* 100, 2495–2504, (2000).

The peroxidase enzyme can be connected to the recognition unit covalently or non-covalently. The peroxidase-containing conjugate marker used in the practice of the present invention is capable of binding to either the specific binding ligand of interest or its corresponding receptor. The recognition unit may be a labeled analog of the specific binding ligand (such as labeled haptenic derivatives of the ligand). In sandwich assays, the labeled immunoreactant can be a labeled receptor for the ligand, or it can be a labeled molecule (such as a labeled anti-antibody) which binds to the receptor (such as an antibody).

The recognition unit and the peroxidase enzyme can be covalently linked together to form the peroxidase-containing conjugate markers using any of a number of known procedures, and many of such reagents are commercially available from a number of sources. Preparatory procedures include those described by Hermanson in "Bioconjugation Techniques" Academic Press 1996 and in U.S. Pat. No. 5,106,732 (Kondo et al).

By "peroxidase" in this application is meant any peroxidative substance (enzymatic or otherwise) which catalyzes the oxidation of a substrate, such as a leuco dye, in the presence of hydrogen peroxide or other oxidant to produce an appropriate signal. Microbial, fungal or plant peroxidases are preferred with horseradish peroxidase being most preferred.

The amount of a peroxidase-containing conjugate marker in an element of this invention can vary widely due to the amount of the other components used in the reaction and the suspected amount of particles in the test sample.

The peroxidase-containing conjugate markers useful in this invention is preferably a peroxidase-labeled hapten derivative of the ligand or a peroxidase-labeled antibody. However, a conjugate of avidin or another specific binding compound with peroxidase also can be used in the practice of this invention. Where the label is on a hapten, for example, it can be a peroxidase-labeled drug, hormone, protein, metabolite, chelate or haptenic derivative of any of these. Examples of such materials include, but are not limited to, peroxidase-labeled haptenic derivatives of digoxin, diphenylhydantoin, phenobarbital, C-reactive protein, a thyronine derivative such as thyroxine, carbamazepine or another analyte described above.

The preferred peroxidase for this invention is horseradish peroxidase. Horseradish peroxidase C (E.C.1.11.1.7) (HRP) is the major peroxidase isozyme isolated from the horseradish (*Armoracia rusticana*). It is a monomeric glycoprotein of 308 amino acids the polypeptide chain having a MW of 33,980 D. There are three neutral carbohydrate side chains and 4 disulphide bridges. The amino acid sequence of the mature protein has been determined. The presence of a pyrrolidonecarboxylyl amino terminus indicates that the protein is probably produced as a precursor form that is processed on secretion. The active form of the enzyme contains a hemin prosthetic group.

The enzyme is particularly stable and is amenable to crosslinking and derivitisation without excessive loss of activity. A further advantage it presents over other enzymatic markers is that some substrates for the enzyme give rise to electron dense products that allow correlation of peroxidase location with cellular ultrastructure using electron microscopy. In addition, horseradish peroxidase is electron dense itself by virtue of the Fe it contains and as a result can act as an E.M. marker in its own right. Particular applications have been found in immunochemistry, where peroxidase cross linked to immunoglobulin is widely used in both ELISA based assay systems and immunocytochemistry. Methods have been described that use either direct crosslinking of peroxidase to the immunoglobulin or indirect crosslinking of biotin labelled immunoglobulin to a streptavidin/horseradish peroxidase complex. Such streptavidin complexes have also found widespread application in nucleic acid hybridzsation methods where biotinylated probe sequences can be localized by sequential incubation with the streptavidin/peroxidase complex and a suitable chromogenic peroxidase substrate. The amino acid sequence of horseradish peroxidase is taught by Welinder, K. G. (Eur. J. Biochem. 96, 483–502 (1979)).

While the method is schematically illustrated with respect to only two cells 4, and 5, the method may be applied for sorting and or separating a plurality of cells (not shown) and is suitable for sorting and/or separating large populations of cells of different types. The cell 4 is different than the cell 5. The cell 4 may be distinguished from the cell 5 based on a detectable difference of at least one characteristic or property on the surface of the cells.

The target particles are suspended/in or covered with a suitable liquid. The probe-bearing particles may be brought in contact with the surface of the gelatin layer by covering the gelatin layer with an amount of liquid, in which the particles are suspended or contained. The particles are allowed to sediment or settle to the surface, either by gravity alone or by centrifugation of the entire support, as well as, the gelatin layer, or the slide or vessel or container or other member which comprises the support and gelatin layer, or by using any other suitable type of method for assisting or accelerating the sedimentation of particles, such as for example, by changing the ionic strength or the pH of the solution in which the particles are suspended by adding suitable salt solutions or buffer solutions, or by using electrophoresis, by attracting the particles to the surface using suitable electrical currents passed between the layer or the substrate and a suitable electrode immersed in the liquid, or by any other suitable method known in the art for accelerating or assisting the sedimentation of particles.

In cases in which the target particles are viable cells, the suspending liquid may typically be a physiological solution or medium adapted for maintaining the viability of the cells at least for the duration of the separation or sorting procedure or for longer time periods. For example, the liquid may be phosphate buffered saline (PBS), or any other suitable physiological solution, or similar medium, known in the art.

The suspension can be buffered with one or more typical buffer systems, including but not limited to, phosphate saline buffer, tris buffer, MES buffer, glycine buffer, and acetate buffer.

The developer contains 1) a phenolic compound and 2) hydrogen peroxide. When the developer is added to the suspension solution containing the peroxidase-containing conjugate marker, a substance is formed in the vicinity of the particle 4 by the development. This substance binds or adheres the settled particles which are in contact with the gelatin surface 2A to the gelatin surface. It is believed that the substance is a polyphenolic compound. Thus, the particle 4 adheres to or becomes effectively attached to the gelatin layer 2. In contrast to the particle 4 which becomes attached to the gelatin layer 2, the particle 5 is not attached to the gelatin layer 2 because the region of the layer 2 which underlies the particle 5 does not produce any substance 6. (FIGS. 1C–1D)

The developer for this invention can be any hydrogen peroxide containing solution. The developer can be aqueous or non-aqueous, buffered or non-buffered. The concentration of hydrogen peroxide in the developer can be from 0.01% (w/v) to 10% (w/v).

The developer must be activated by contact with at least one phenolic compound. The phenolic compound may be included in the suspension solution or added to the suspension solution after the suspension is poured over gelatin surface. The phenolic compound may be added in its own solution. The phenol must be added prior to or simultaneously with the hydrogen peroxide.

The phenolic compound is represented by the following general formula:

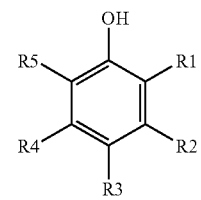

where R1, R2, R3, R4, R5 may be the same or different and may be hydrogen, a substituted or unsubstituted linear or branched alkyl group of 1 to 10 carbon atoms (such as methyl, ethyl, n-propyl, isopropyl, t-butyl, hexyl, decyl, benzyl, methoxymethyl, hydroxyethyl, ethyleneoxy, iso-butyl, and n-butyl), a substituted or unsubstituted aryl group of 6 to 14 carbon atoms (such as phenyl, naphthyl, anthryl, tolyl, xylyl, 3-methoxyphenyl, 4-chlorophenyl, 4-carbomethoxyphenyl and 4-cyanphenyl), a substituted or unsubstituted cycloalkyl group of 5 to 14 carbon atoms such as cyclopentyl, cyclohexyl, and cyclooctyl), a substituted or unsubstituted heterocyclic group (such as pyridyl, pyrimidinyl and furanyl), or a solubilizing group, or a halogen atom of fluoride, chloride, bromide, iodide. Preferably, at least one of the R groups is or contains a solubilizing substituent that is generally negatively charged such as an ionized acidic group. Examples of these solubilizing groups include, but are not limited to, carboxylic acid, sulfonic acid, phosphonic acid, sulfonamide, and hydroxy groups (and their corresponding salts), other solubilizing substituents which may be present on one or more R groups are polyethylenoxy, amino groups and others readily apparent to one skilled in the art. R1 and R2, and R3 and R4, may be joined by sufficient number of carbon, nitrogen, and sulfur atoms to form, independently, a five or six-member ring.

Representative phenolic compounds useful in the present invention are illustrated by the following structures:

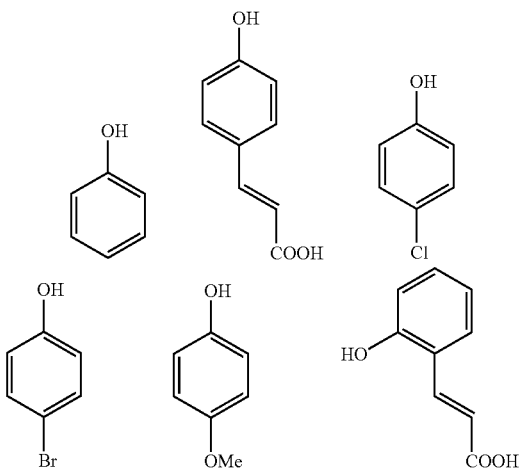

After the target particles are labeled with the conjugate markers, the suspension containing marked target particles as well as non-target particles can be poured over a gelatin coated surface.

Normally, gelatin is coated onto a support and gelation occurs through a process by which gelatin solutions or suspensions of gelatin and other materials form continuous three-dimensional networks that exhibit no steady state flow. This can occur in polymers by polymerization in the presence of polyfunctional monomers, by covalent cross-linking of a dissolved polymer that possesses reactive side chains and by secondary bonding, for example, hydrogen bonding, between polymer molecules in solution. Polymers such as gelatin exhibit thermal gelation which is of the latter type. The process of gelation or setting is characterized by a discontinuous rise in viscosity. (See, P. I. Rose, "The Theory of the Photographic Process", $4^{th}$ Edition, T. H. James ed. pages 51 to 67).

The gelatin substrate described in this invention can either be coated as is on any solid support, or with one or a combination of multiple hardening agents mixed in the gel. The level of the hardening agent should be from 0 to 20 wt. %, and preferably 0.5 to 8 wt. %, of the total gelatin coated.

There are two types of gelatin: acid pretreated and alkaline pretreated. The preferred gelatin is alkaline pretreated gelatin from bovine bone marrow, but gelatin can also come from other sources.

The gelatin is coated on a base called the "support" herein. Supports of choice for this invention can be organic, inorganic or biological. Some commonly used support materials include glass, plastics, metals, and semiconductors. The support can be transparent or opaque, flexible or rigid. The gelatin surface for this invention can be flat or slightly curved. In some cases, the support can be a porous membrane e.g. nitrocellulose and polyvinylidene difluoride, and the gelatin can be deposited onto the membrane by physical adsorption. The support 1 is preferably a flat support, but other types of support, such as but not limited to, curved supports, stepped supports, and other supports having a surface which is not flat or is only partially flat may be used. The support 1 (only a portion of which is illustrated in FIGS. 1A–1F), may be a part of a suitable member, such as but not limited to, a microscope slide (not shown), a Petri dish (not shown), an open container or vessel (not shown), or a covered container or vessel (not shown), or the like, depending on the specific implementation or preferred embodiment of the invention used. The support 1 is preferably made from a transparent substance, such as, but not limited to glass, quartz, or a suitable plastic material, but other substances or compositions may also be used. However, the material from which the support is made may also be opaque, or partially opaque, depending on the specific implementation or preferred embodiment of the present invention which is being used, and on the particular type of optical system used for implementing the invention, such as but not limited to, in optical systems using epi-illumination or reflected light.

Coating methods are broadly described by Edward Cohen and Edgar B. Gutoff in Chapter 1 of "Modern Coating And Drying Technology", (Interfacial Engineering Series; v.1), (1992), VCH Publishers Inc., New York, N.Y. In general, a fluid coating composition contains a binder, a solvent to dissolve or suspend the components, and optional additives such as surfactants, dispersants, plasticizers, biocides, cross-linking agents for toughness and insolubility, and conductive materials to minimize static buildup. All the components are mixed and dissolved or dispersed, and the coating fluid is sent to an applicator where it is applied to a substrate by one of several coating techniques. Heat is then applied to the coating to evaporate the solvent and produce the desired film, or the coating is solidified by the action of ultraviolet radiation or an electron beam.

The most suitable coating method—including the coating speed—will depend on the quality and functionality desired and the materials being used, e.g., the substrate, the solvent, weight and viscosity of the coating, etc. For a single layer format, suitable coating methods may include dip coating, rod coating, knife coating, blade coating, air knife coating, gravure coating, forward and reverse roll coating, and slot and extrusion coating.

Coating speed can also be an important determinant in the choice of coating method. Although most methods can be used at low speeds, and all methods have a limiting upper speed, some work better at higher speeds. Curtain coating requires a minimum flow to maintain the integrity of the curtain. Therefore, this method is limited to higher speeds if a thin coating is to be obtained. In slide coating of multiple layers, interfacial instabilities are more likely to occur on the slide when the layers are very thin. Higher speeds, with their higher flows and thicker layers on the slide, tend to avoid these instabilities. See, p. 12, "Modern Coating and Drying Technology", supra.

The gelatin has a laydown of 0.2 to 100 grams per square meter; preferably 10 to 50 grams per square meter.

Any well known coating method, such as particle coating or curtain coating, can be used to prepare the gelatin substrate. The gelatin could be coated with any other coating aids such as surfactants and thickeners to adjust its physical property. The gelatin used in the invention may be chemically modified either before, during or after the coating process to create more chemical functionalities that can react or interact with biologically active molecules or assemblies intended to be attached on this substrate.

The separation of the cells may now be performed by suitably washing the gelatin layer in such a way that the target particles which are not attached to the gelatin layer, are removed or carried away by a suitable washing liquid applied to the gelatin layer, while the adhered target particles remain attached to the layer. The layer may be washed by additional amounts of a liquid having the same composition as the suspending liquid (preferably without the developer, to minimize the time of exposure of the cells to the developer). Alternatively, the washing may be accomplished by a liquid having a different composition than the suspending liquid. The washing step washes the surface of the layer, carries away the non-adhering cells and leaves behind the target cells adhered to the layer.

FIG. 1C illustrates the layer 2 and the cell 4 adhering to the gelatin surface 2A after the washing. The cell 5 is not illustrated in FIG. 1 C since it has been washed away by the washing step. The washing liquid or fluid (not shown) including the cell 5 (not shown) may be collected for further utilization. Alternatively, the washing fluid may be discarded.

The washing conditions may have to be suitably adapted to ensure a good separation of the cells. Thus, the washing parameters, including the composition of the washing fluid, the total amount or volume of the washing fluid used, the temperature of the washing fluid, the washing rate or flow rate of the washing fluid (expressed as the volume of washing fluid per time unit), the degree of turbulence in the washing fluid, and other washing parameters, may have to be controlled to ensure that all or most of the non-adhering cells (such as, for example, the cell 5 of FIG. 1B) will be removed from the gelatin layer 2 in the washing step.

In accordance with one preferred embodiment of the present invention, the identification of the particle may be visually performed. For example, the support may be a part of a microscope slide, which is visually inspected using an appropriate microscope, or other suitable microscopy devices. The user of the microscope visually observes the target particles and visually identifies the particles. If more than one type of target particle is present, the particles may be differentiated with respect to one or more property, to make them uniquely observable and countable, so that multiple particles may be detected at the same time. In one embodiment, illustrated in FIGS. 1A–1D, the cell 4 has unique surface characteristics that can be detected by a marker conjugated to a peroxidase while the cell 5 does not have such characteristics.

The target particles attached to the gelatin surface can be quantified by simply counting the number of particle on the surface or by an automatic imaging method to analyze the number of particles on the surface.

It is further noted that, while the optical system or microscope used for implementing some preferred embodiments of the present invention may use trans-illumination of the target particles, other methods of visualization or different methods of illumination may be used for visualizing and identifying the target particles. For example, among the methods and techniques which may be used to visualize and/or identify or distinguish different particles are dark field illumination, epi-illumination, phase-contrast microscopy, differential interference contrast microscopy (DIC), polarization microscopy, multi-spectral or hyper-spectral microscopy involving the acquisition and analysis of pixel level spectrogram data as is known in the art, and any other suitable microscopy methods known in the art which may be adapted for use with the methods of the present invention.

Preferably, overlap of the particles should be avoided by proper adjustment of number of the particles to avoid or minimize the adhering of the "wrong" particles to the gelatin surface. The number of the particles is preferably optimized to avoid such undesirable adhering of particles. However, the particle number should be sufficiently high to allow the practical identification of the particles. Thus, the actual initial number of particles in the fluid suspension applied to the gelatin layer 2 may be a compromise which practically avoids contaminating undesired particles, while still ensuring high yield of the required particles to be identified. The initial number particles may also depend on the type and morphological parameters of the particles, and on other factors. For certain applications in which a single particle, or very few particles is sufficient, a very low initial number of particles may be utilized in implementing the method of the present invention.

After selectively immobilizing target particles on the gelatin surface followed by subsequent removal of non-target particles, the target particles can be recovered for further analysis. This recovery process is especially important for living cell sorting applications where the separated target cells can be subjected to additional analysis and characterization.

The immobilized particles may be recovered from the surface, if required, by an appropriate treatment (such as, but not limited to, treatment with a chemical) which may detach the immobilized particle(s) from the coated surface. In one embodiment, when the particles to be sorted or separated are isolated eukaryotic or prokaryotic cells (either viable or dead), the cells may typically adhere or bind to surface by physical, or chemical-physical, or chemical interactions between the surface and molecules on the surface of the particle(s), such as, for example, surface proteins exposed on the outer side of the cell's membranes. In an exemplary case, detachment of the adhering cells from the gelatin surface may be performed by subjecting the cells to a proteolytic enzyme, such as, but not limited to, trypsin, pepsin, papain, or the like, which cuts the extracellular proteins that bind the cells to the gelatin surface, thus enabling harvest of the cells for further use or analysis. However, other particle detachment methods may be used for various types of particles. Examples of other particle detachment methods may be, but are not limited to, the selective dissolution of the matrix constituting the coated layer in order to release the particle(s), and/or physical means like sonication to release the particle(s).

After the washing is completed, the cell 4 may be recovered by suitably dissociating it from the layer 2. For example, a fluid 7 such as, but not limited to, a solution containing a proteolytic enzyme, such as, for example, trypsin, pepsin, papain or other suitable proteolytic enzymes known in the art, may be applied to the gelatin layer 2. The layer 2 and the cells adhering to it (such as, but not limited to the cell 4), may then be incubated with the fluid 7 for a time period sufficient for the dissociation of the cell 4 from the gelatin surface 2A. The dissociation of the adhered cell by the proteolytic enzyme is believed to occur via the degradation or modification of the surface protein molecules on the surface of the cell 4 or on the surface 2A of coated gelatin as well as partial degradation of gelation surface 2A. As a result, the cell 4 may dissociate from the layer 2 (as illustrated in FIG. 1D). Or, the bond between the cell 4 to the gelatin surface may be sufficiently weakened to enable the cell 4 to detach from the layer 2 with subsequent washings which removes the cell 4 or any other cells (not shown) which were previously immobilized on the layer 2. The cell 4 or other cells (not shown) which were dissociated and washed out from the layer 2 may now be collected or harvested in the washing fluid. Alternatively, the cell 4 may be collected under visual control by observing the layer 2 under the microscope and using a suitable micro-pipette (not shown) or another suitable suction device to harvest the cell 4 or other cells that need to be collected. Briefly turning to FIG. 1D, the cell 4 is shown as being dissociated from the layer 2 and the gelatin surface 2A included in the layer 2 and is floating free in the fluid 7.

If the cell 4 is required for further use, and if it includes proteinacious material, the proteolytic enzyme may have to be neutralized by means known in the art, such as, but not limited to, the addition of serum or a suitable tissue culture medium, followed by a wash, or by any other suitable neutralizing or washing method known in the art. Similar neutralization and/or washing methods may be used when the separated or sorted particles are of biological origin or contain proteinacious materials, such as but not limited to when the particles to be separated are bacteria, subcellular particles such as, but not limited to mitochondria, cell membranes or fragments, genes or fragments.

The invention is now described in reference to FIGS. 1A–1F which are schematic diagrams illustrating a particle sorting and/or separating method of the invention in accordance with one preferred embodiment of the present invention. FIG. 1A shows a support 1 coated with a layer of gelatin 2.

The gelatin layer 2 has a surface 2A which is in contact with a fluid or liquid 3 which covers the surface 2A or a portion of the surface 2A. The surface 3A schematically represents the boundary or interface between the liquid 3 and the air or gas overlying the liquid 3. Two different cells (or particles) 4 and 5 are illustrated as being in contact with the surface 2A of the gelatin layer 2. The cells 4 and 5 are immersed in or covered with a suitable liquid 3 (it is noted that for the sake of clarity of illustration, only a part of the layer of liquid 3 is illustrated in FIGS. 1A–1D). The cells 4 and 5 may be brought in contact with the surface 2A of the gelatin layer 2 by covering the layer 2 with an amount of the liquid 3 in which the cells 4 and 5 are suspended or contained and allowing the cells 4 and 5 to sediment or settle to the surface 2A. Once the cells 4 and 5 settled in liquid 3, the developer added in the liquid 3 develops a substance 6 that generates adhesive forces between cell 4 and surface 2A (see FIG. 1 B). The separation of the cells may now be performed by suitably washing the gelatin layer 2 in such a way that the cell 5 which is not attached to the gelatin layer 2, is removed or carried away by a suitable washing liquid (not shown) applied to the gelatin layer 2 while the adhered cell 4 remains attached to the layer 2. After the washing is completed, the cell 4 may be detected, identified and recovered by suitably dissociating it from the layer 2.

The invention can be better appreciated by reference to the following specific embodiments.

EXAMPLES

Preparation of Gelatin Coating

Solution A: 147.8 g of 35% gelatin solution, 963 g of water, 46.8 g of 9% siloxanes & silicones, di-Me, 2.5 g of 4.97% 1H-1,2,4-Triazolium, 1,4-diphnyl-3-(phenylamino)-inner salt, 3.55 g of 7.6% 2,4-Pentanediol, 2-methyl, and 36 g of 6.68% Ethanesulfonic acid, 2(2-(2-(4-(1,1,3,3-tetramethyl butyl) phenoxy) ethoxy)ethoxy)-, sodium salt.

Solution B: 106.2 g of 1.79% 1,1'-(methylene bis(sulfonyl) bis-ethene and 1,094 g of water.

Solution A and solution B were coated at 29.71 mL/square meter and 15.01 mL/square meter, respectively. The two solutions were delivered to and mixed at the coating hopper. The resulting coating was then dried. The coating contained 1.399 g of gelatin/square meter.

Preparation of Target Particles:

Spin down 500 μL of 10 μM magenta colored carboxy modified polystyrene particles (1% w/w) in a 1.5 mL eppendorf tube for 3 minutes at 13000 RPM. Carefully remove supernatant and add 1 mL of 0.05 M acetate buffer, with 0.05% (w/w) Tween 20 pH 5.0. Vortex to homogenize. Repeat acetate buffer wash a second time and remove supernatant. Add 1 mL of the following solution: 0.1 M N-hydroxysuccinimide, (NHS) and 0.05 M 1-[3(dimethylamino)propyl]-3-ethylcarbodiimide hydrochloride (EDC) dissolved in 0.05 M acetate buffer. (115 mg NHS, 96 mg EDC, 10 mL acetate buffer). Vortex to homogenize and react for 1 hour at room temperature with agitation. Spin down particles for three minutes at 13000 RPM, remove supernatant and wash with acetate buffer, removing supernatant. Add 1 mL of a 1 mg/mL solution of anti-mouse IgG-horseradish peroxidase conjugate in acetate buffer to particle pellet. Vortex to homogenize and react for 1 hour at room temperature with agitation. Wash particles three times in PBS buffer with 0.05% (w/w) Tween 20, pH 7.4.

Preparation of Non Target Particles

Spin down 500 uL of 10 uM non-colored (white) carboxy modified polystyrene particles (1% w/w) in a 1.5 mL eppendorf tube for 3 minutes at 13000 RPM. Carefully remove supernatant and add 1 mL of 0.05 M acetate buffer, with 0.05% Tween 20 pH 5.0. Vortex to homogenize. Repeat acetate buffer wash a second time and remove supernatant. Add 1 mL of the following solution: 0.1 M (NHS) and 0.05 M (EDC) dissolved in acetate buffer. (115 mg NHS, 96 mg EDC, 10 mL acetate buffer). Vortex to homogenize and react for 1 hour at room temperature with agitation. Spin down particles for three minutes at 13000 RPM, remove supernatant and wash with acetate buffer, removing supernatant. Add 1 mL of a 1 mg/mL solution of bovine serum albumin (BSA) in acetate buffer to particle pellet. Vortex to homogenize and react for 1 hour at room temperature with agitation. Wash particles three times in PBS buffer with 0.05% tween 20, pH 7.4.

Figure 3:
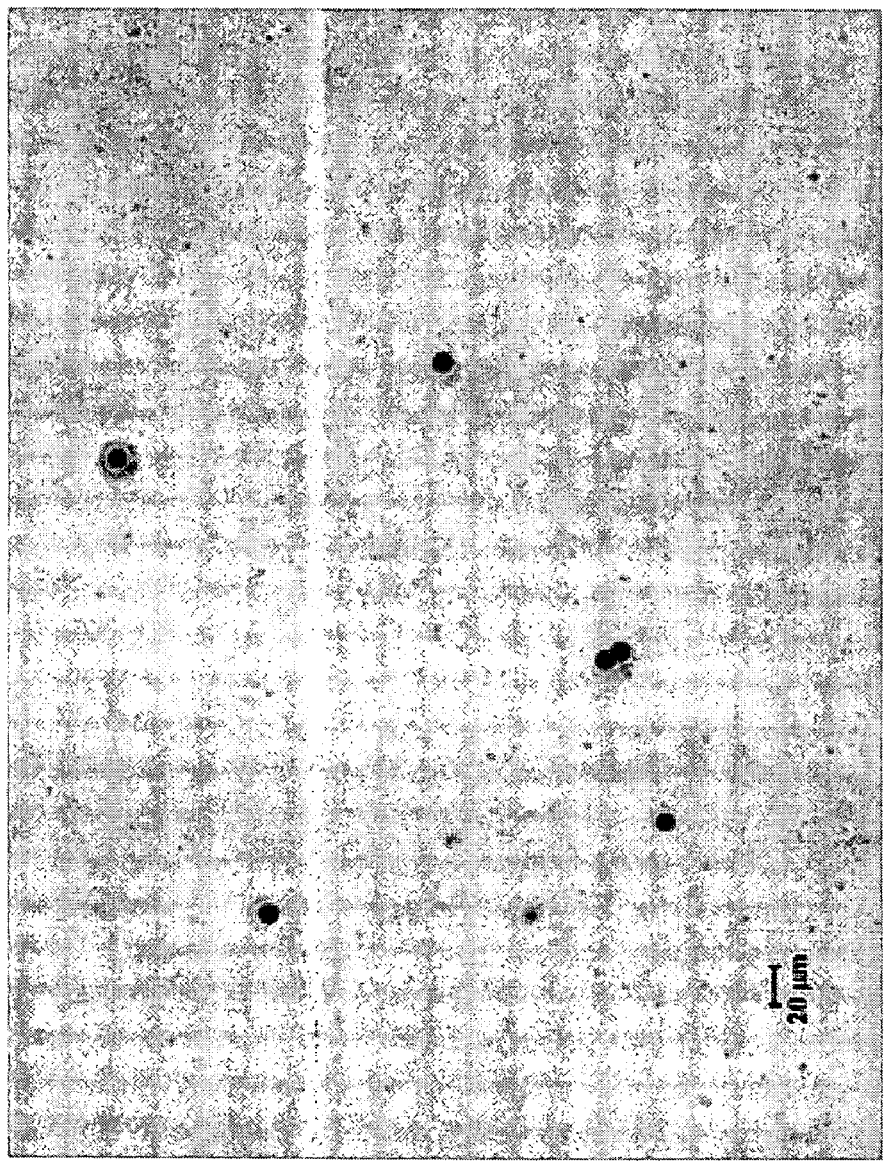
FIG. 3 shows a microscopic image of target particles after separation.

Mixed Particle Preparation and Separation:

In a 1.5 mL eppendorf tube combine: 10 μL of 0.1% (w/w) Target particles (antimouse IgG-HRP modified particles), 90 μL of 1.0% (w/w) Non-Target particles (BSA), 900 uL of 0.75 mg/mL coumaric acid in 0.05 M Tris buffer pH 8.5. Mix well. Apply particle mixture over a 25 mm×76 mm piece of gel coated substrate and wait five minutes for particles to settle (FIG. 2). Add 100 μL of 0.4% hydrogen peroxide solution in water, wait 5 minutes. Pour approximately 1 L of distilled water over the gelatin coated substrate to remove any unattached particles. Observe particles under a microscope (100× magnification). The gelatin coating surface contains over 90% magenta colored target particles and no non-target white particles on the surface as shown in FIG. 3. The separated magenta colored target particles are recovered by sonicating the coating in water for 30 seconds.

The invention has been described in detail with particular reference to certain preferred embodiments thereof, but it will be understood that variations and modifications can be effected within the spirit and scope of the invention.

The invention claimed is:

1. A method of particle separation comprising:
    preparing a suspension of particles containing at least one recognizable target particle in a suspending solution;
    labeling said at least one recognizable target particle in said suspending solution with a conjugate marker, wherein said conjugate marker comprises at least one recognition unit specific for said recognizable target particle and at least one peroxidase enzyme;
    contacting a gelatin surface with said suspending solution;
    adding developer comprising oxidant to said suspending solution in contact with said gelatin surface in the presence of phenol to attach said recognizable target particle to said gelatin surface;

washing said gelatin surface to remove unattached particles.

2. The method of claim 1 wherein said target particle is organic or inorganic.

3. The method of claim 1 wherein said target particle is a cellular or subcellular particle.

4. The method of claim 1 wherein said target particle is circular, spherical, rectangular, or elliptical.

5. The method of claim 1 wherein said target particle is recognizable by characteristics of the particle itself.

6. The method of claim 1 wherein said target particle is recognizable through a specific marker attached to said target particle.

7. The method of claim 1 wherein said suspending solution is an aqueous solution.

8. The method of claim 7 wherein said suspending solution is buffered.

9. The method of claim 1 wherein said suspending solution further comprises phenol.

10. The method of claim 1 wherein said recognition unit is an antibody, antigen, or ligand.

11. The method of claim 1 wherein said recognition unit has an affinity binding constant to the target analyte of no less than $10^{-6} M^{-1}$.

12. The method of claim 1 wherein said recognition unit is a nucleic acid or nucleic acid ligand.

13. The method of claim 1 wherein said recognition unit is a protein scaffold or synthetic molecular moiety capable of recognizing a specific DNA sequence.

14. The method of claim 1 wherein said peroxidase is connected to the recognition unit covalently.

15. The method of claim 1 wherein said peroxidase is connected to the recognition unit non-covalently.

16. The method of claim 1 wherein said peroxidase is horseradish peroxidase (HRP).

17. The method of claim 1 wherein said gelatin is coated onto a support.

18. The method of claim 17 wherein said support is organic, inorganic or biological.

19. The method of claim 17 wherein said support is glass, quartz, plastics, metals, semiconductors, a porous membrane.

20. The method of claim 1 wherein said gelatin further contains hardener.

21. The method of claim 1 wherein said gelatin has a laydown of from 0.2 to 100 grams per square meter.

22. The method of claim 1 wherein said gelatin has a laydown of from 10 to 50 grams per square meter.

23. The method of claim 1 wherein said developer contains hydrogen peroxide.

24. The method of claim 1 wherein the concentration of said hydrogen peroxide in said developer is from 0.01% (w/v) to 10% (w/v).

25. The method of claim 1 wherein said developer is aqueous.

26. The method of claim 1 wherein said developer is buffered.

27. The method of claim 1 wherein said developer further contains phenol.

28. The method of claim 1 wherein said phenol is added prior to or simultaneously with said developer.

29. The method of claim 1 wherein said phenol is represented by the following general formula:

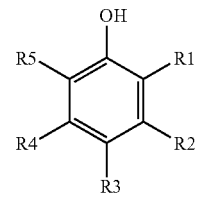

where R1, R2, R3, R4, R5 are independently a hydrogen, a substituted or unsubstituted linear or branched alkyl group of 1 to 10 carbon atoms, a substituted or unsubstituted aryl group of 6 to 14 carbon atoms, a substituted or unsubstituted cycloalkyl group of 5 to 14 carbon atoms, a substituted or unsubstituted heterocyclic group, a solubilizing group, or a halogen atom of fluoride, chloride, bromide, iodide.

30. The method of claim 29 wherein at least one of R1, R2, R3, R4, R5 is or contains a solubilizing substituent that is generally negatively charged.

31. The method of claim 1 wherein said phenol is represented by at least one of the following structures:

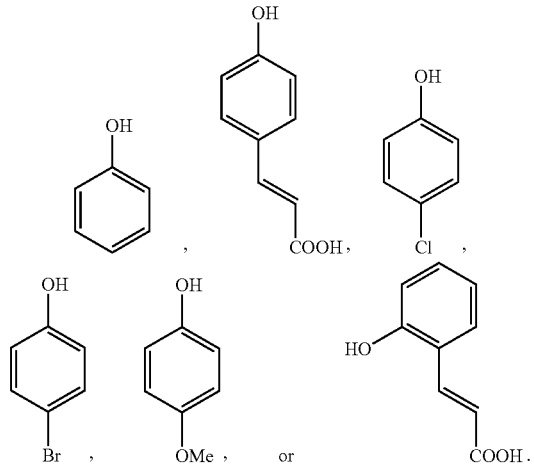

32. The method of claim 1 wherein said washing is aqueous.

33. The method of claim 1 further comprising:
detaching said attached target particle; and
recovering said detached target particle.

34. The method of claim 33 wherein said detaching occurs by treatment with a chemical which may detach said attached target particle from said gelatin surface.

35. The method of claim 33 wherein said detaching occurs by subjecting the attached target particle to a proteolytic enzyme.

36. The method of claim 35 wherein said proteolytic enzyme is trypsin, pepsin, or papain.

37. The method of claim 33 wherein said detaching occurs by selective dissolution said gelatin surface in order to release said attached target particle.

38. The method of claim 33 wherein said detaching occurs by sonication to release said attached particle.

39. The method of claim 33 wherein said recovering occurs by removal of said detached target particle from additional washing fluid.

40. The method of claim 33 wherein said recovering occurs by collection through a suction device under visual control.

41. The method of claim 40 wherein said suction device is a micro-pipette.

42. The method of claim 33 further comprising detecting said attached target particle prior to said detaching and said recovering.

43. The method of claim 1 further comprising detecting said attached target particle.

44. The method of claim 43 wherein said detecting is visual inspecting.

45. The method of claim 44 wherein said visual inspecting utilizes a microscope.

46. The method of claim 43 wherein said detecting is automatic imaging.

47. The method of claim 43 wherein said detecting is dark field illumination, epi-illumination, phase-contrast microscopy, differential interference contrast microscopy (DIC), polarization microscopy, multi-spectral or hyper-spectral microscopy.

48. The method of claim 43 wherein said detecting is full-frame image capture.

* * * * *